US00PP17295P2

(12) United States Plant Patent
Hansen

(10) Patent No.: US PP17,295 P2
(45) Date of Patent: Dec. 19, 2006

(54) ***HOSTA* PLANT NAMED 'CATHEDRAL WINDOWS'**

(50) Latin Name: *Hosta hybrida*
Varietal Denomination: Cathedral Windows

(75) Inventor: Hans Andrew Hansen, Waseca, MN (US)

(73) Assignee: Shady Oaks Nursery, LLC, Waseca, MN (US); part interest ( * ) Notice: Subject to any disclaimer, the term of this patent is extended or adjusted under 35 U.S.C. 154(b) by 0 days.

(21) Appl. No.: 11/225,909

(22) Filed: Sep. 14, 2005

(51) Int. Cl.
*A01H 5/00* (2006.01)

(52) U.S. Cl. ..... Plt./353

(58) Field of Classification Search ..... Plt./353
See application file for complete search history.

(56) References Cited

PUBLICATIONS http://www.plantdelights.com/Catalog/Spring/Detail/06600.html.*

* cited by examiner

*Primary Examiner*—Wendy Haas
(74) *Attorney, Agent, or Firm*—Penny J. Aguirre

(57) ABSTRACT

A new cultivar of *Hosta* named 'Cathedral Windows', derived as a sport of 'Stained Glass' and characterized by wide dark green margins and bright yellow-green centers that intensify in color in summer. 'Cathedral Windows' blooms in late July to late August with nearly white flowers held above the foliage on erect scapes.

2 Drawing Sheets

Botanical classification: *Hosta hybrida.*
Cultivar designation: 'Cathedral Windows'.

BACKGROUND OF THE INVENTION

The present invention, *Hosta* 'Cathedral Windows', relates to a new and distinct cultivar of *Hosta*, botanically known as a *Hosta hybrida*, hereinafter referred to as 'Cathedral Windows'.

'Cathedral Windows' originated as a chemically induced mutation of *Hosta* 'Stained Glass' in 2000 in Waseca, Minn.

Asexual reproduction of the new cultivar was first accomplished by the inventor by division in Waseca, Minn. in summer of 2004. Asexual reproduction of the new cultivar by division and tissue culture has shown that the unique features of 'Cathedral Windows' are stable and reproduced true to type in successive generations.

SUMMARY OF THE INVENTION

The following traits have been repeatedly observed in trials in Minnesota for a period of five years and represent the characteristics of the new cultivar. These attributes in combination distinguish 'Cathedral Windows' as a new and unique cultivar of *Hosta.*

1. The foliage of 'Cathedral Windows' is variegated with wide dark green margins and bright yellow-green margins that intensify during the summer. The margins of 'Cathedral Windows' are wider than those of the parent plant, 'Stained Glass' and comprise an average of two-thirds of the leaf area.
2. The leaf aspect of 'Cathedral Windows' is dome shaped, the leaf aspect of 'Stained Glass' is nearly flat.
3. 'Cathedral Windows' is moderate to vigorous grower and reaches about 48 cm in height and 86 cm in width.

4. 'Cathedral Windows' blooms in late July to late August with nearly white flowers held above the foliage on erect scapes.

BRIEF DESCRIPTION OF THE DRAWING

The accompanying colored photographs illustrate the overall appearance and distinct characteristics of the new *Hosta*. The photographs were taken in July of mature plants of 'Cathedral Windows' as grown outdoors in Waseca, Minn. for a period of five years.

Figure 1:
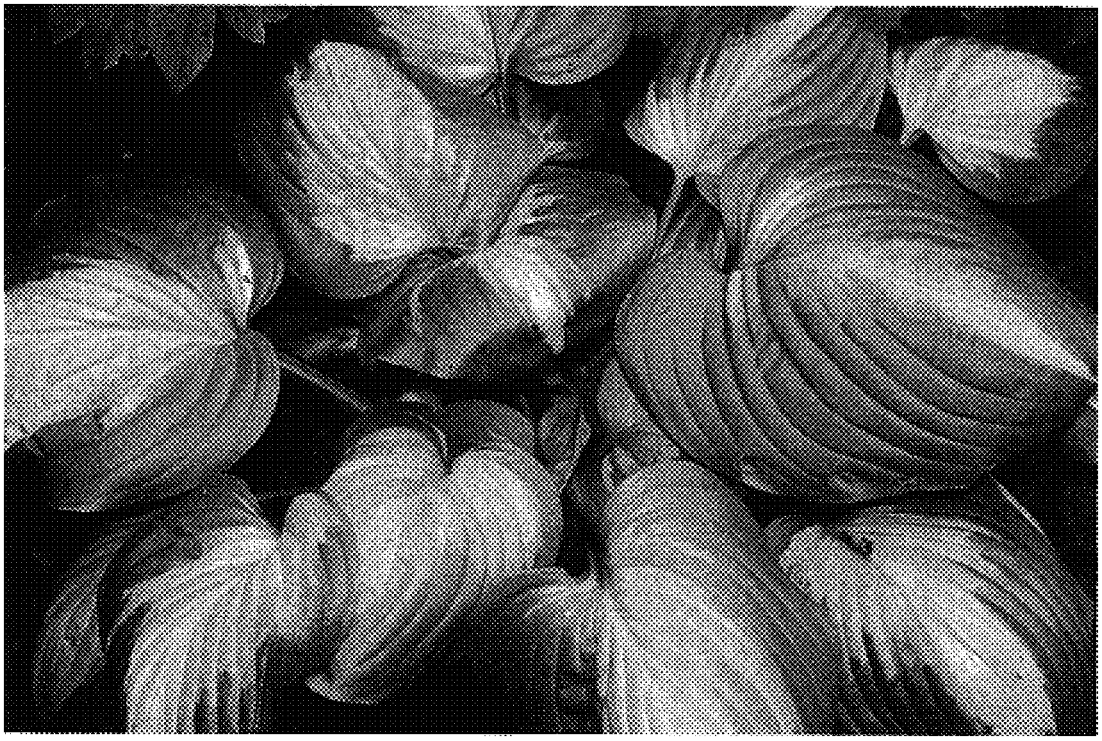
FIG. 1 provides an overall view of the plant habit and the summer foliage of the new cultivar, 'Cathedral Windows'.
Figure 2:
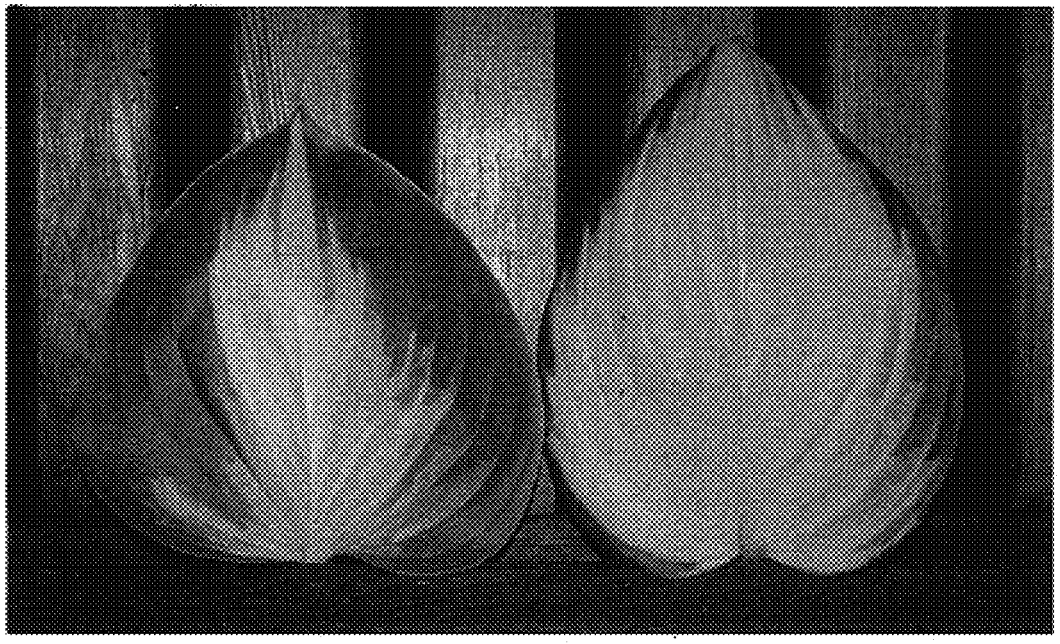
FIG. 2 provides a comparison between a leaf of 'Cathedral Windows' (left) and a leaf of 'Stained Glass' (right) and illustrates the differences in variegation pattern.
Figure 3:
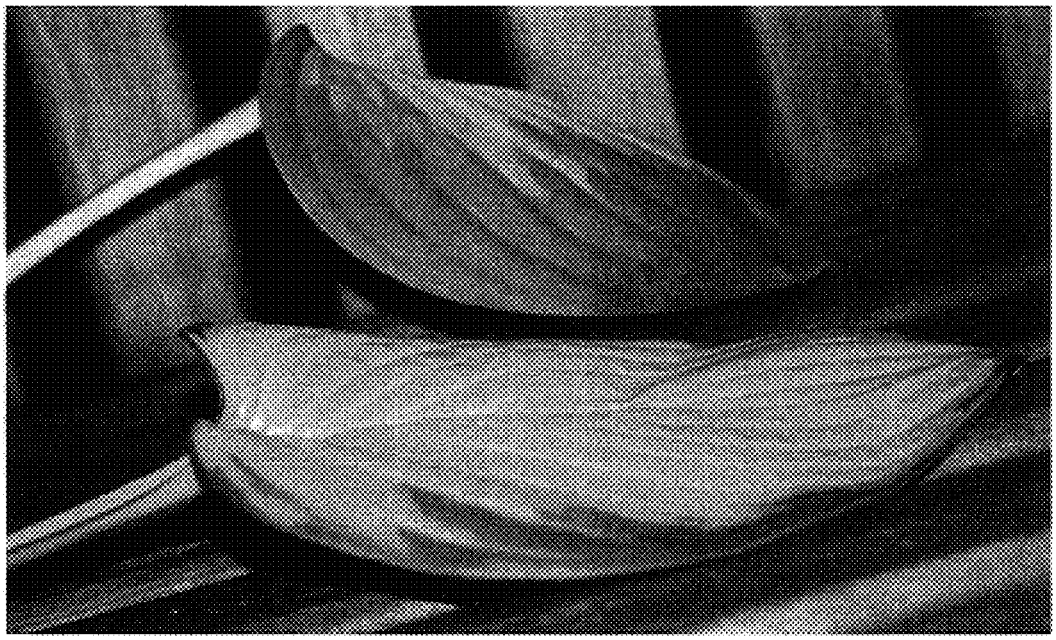
FIG. 3 provides a comparison between a leaf of 'Cathedral Windows' (top) and a leaf of 'Stained Glass' (bottom) and illustrates the differences in leaf aspect.

The colors in the photographs are as close as possible with the photographic and printing technology utilized and combined with the color values cited in the detailed botanical description accurately describe the colors of the new *Hosta.*

DETAILED BOTANICAL DESCRIPTION OF THE PLANT

The following is a detailed description of five year-old plants of the new cultivar as grown outdoors in Waseca, Minn. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'Cathedral Windows' is a cultivar of *Hosta hybrida*.

Parentage: Naturally occurring sport of *Hosta* 'Stained Glass' (not patented).

General description:

*Blooming period.*—Blooms for about 3 to 4 weeks from late July to late August.

*Plant habit.*—Herbaceous perennial, clump-forming, mounded habit.

*Height and spread.*—Reaches about 48 cm in height (excluding flower scapes) and about 86 cm in width.

*Hardiness.*—U.S.D.A. Zones 3 to 8.

*Culture.*—Light to full shade, moist soils of moderate fertility.

*Diseases and pests.*—Above average substance confers some resistance to slugs. No susceptibility or resistance to diseases or other pests has been observed for 'Cathedral Windows'.

*Root description.*—Freely branched, fleshy.

*Propagation.*—*In vitro* propagation is the preferred method utilizing typical methods for *Hosta*, division is also possible.

*Root development.*—Rooted transplants from tissue culture fully develop in a 96-cell liner in about 6 to 8 weeks in a greenhouse with average temperatures of about 70° F.

*Growth rate.*—Moderate to vigorous.

Foliage description:

*Leaf shape.*—Broadly ovate.

*Leaf division.*—Simple.

*Leaf base.*—Cordate.

*Leaf apex.*—Cuspidate.

*Leaf venation.*—12 pairs of veins, camptodrome pattern, impressed on upper surface and raised on lower surface, color matches foliage coloration.

*Leaf margins.*—Entire, flat without undulations, slightly undulated when mature.

*Leaf attachment.*—Petiolate.

*Leaf arrangement.*—Basal, radiate spirally from base.

*Leaf surface.*—Glabrous on upper and lower surface in spring, slightly shiny on upper and glaucous on lower surface on summer foliage.

*Leaf substance.*—Average.

*Leaf orientation.*—Cupped downward and held nearly horizontal on petioles held upright or up to about a 45° angle to center.

*Leaf variegation pattern.*—Margins comprise about one half to two thirds of the leaf area on mature leaves and average about 6 cm in width, the centers are primarily elliptic in shape with addition narrower areas radiating from the center pattern, a small intermediate area exists in an irregular pattern between the boundaries of the margins and centers on the summer foliage. The variegation is more distinct on summer foliage.

*Leaf color.*—Spring foliage, upper surface; centers 144B, margins 137B, lower surface; centers 137D, margins 137C. Summer foliage, upper surface; centers N144A to N144B, margins color between 137A with hint of 144A, intermediate areas primarily 144A, lower surface; centers 145A to 145B, margins 138A, intermediate areas closest to 139D.

*Leaf size.*—Average of 22 cm in length, average of 22 cm in width (mature leaves).

*Leaf quantity.*—About 5 to 7 per shoot (eye).

*Petiole size.*—About 40 cm in length, about 2 cm in width.

*Petiole color.*—Variegation that radiates into leaf blade, inner surface 144B with edges of 137A with hint of 144A, outer surface 145B with margins 137A with hint of 144A.

*Petiole surface.*—Glabrous on spring foliage, shiny on summer foliage.

*Petiole shape.*—Sulcate.

Flower scape description:

*Scape shape.*—Round, solid.

*Scape number.*—One per mature eye under normal growing conditions.

*Scape posture.*—Held nearly vertical.

*Scape size.*—About 110 cm in length, about 7 mm in width.

*Scape color.*—144A.

*Scape surface.*—Glabrous, slightly glaucous.

*Leaf bracts.*—About 2, about 4 cm in length and 1.5 cm in width, 144A to 144B in color (upper and lower surface), broadly ovate in shape, glabrous to slightly glaucous in texture, clasping around scape.

Flower description:

*Inflorescence type.*—Terminal racemes of single tubular-shaped flowers.

*Lastingness of inflorescence.*—About 3 to 4 weeks from first opening bloom to fading of last opening bloom, individual blooms last about 1 day.

*Flower shape.*—Tubular.

*Flower number.*—About 28 per scape.

*Flower internode length.*—Up to about 2 cm.

*Flower fragrance.*—Fragrant.

*Flower bud shape.*—Spathulate.

*Flower bud size.*—Up to about 5.5 cm in length and 1.8 cm in diameter.

*Flower bud color.*—Tube portion 155B, expanded region 155B (whiter) with slight blush or 85D and 85C.

*Flower size.*—About 5 to 7 cm in length and about 2.5 cm in diameter with tube portion an average of 2 cm in length and 5 mm in diameter and expanded portion about 4.5 cm in length and 2.5 cm in diameter.

*Flower color.*—Whiter than 155B with shading of 85D.

*Pedicels.*—About 8 mm in length, 3 mm in diameter, 155C in color with base of 144D.

*Perianth features.*—Comprised of 6 tepals, 3 interior and 3 exterior, fused in tube region and about one third of expanded region, one third of expanded region is overlapping and one third is separate.

*Tepal shape.*—Oblanceolate.

*Tepal size.*—About 6 cm in length, about 1.8 cm in width.

*Tepal color.*—Whiter than 155B with shading of 85D and tips of 85C.

*Tepal texture.*—Glabrous.

*Floral bracts.*—1 per flower, broadly ovate in shape, glabrous to slightly glaucous surface, 144A to 144B in color (upper and lower surface), up to 3 cm in length and 2 cm in width, acute apex, clasping base.

Reproductive organs:

*Gynoecium.*—1 Pistil. Style is about 5.5 cm in length, 1 mm in width and 155B in color. Stigma is 3-lobed, 8A in color and 0.75 mm in diameter. Ovary is superior, compound, composed of 3 locules, oblong in shape, 8 mm in length, 2 mm in width and 144D in color.

*Androecium.*—6 stamens, filament is 155B in color, about 5 cm in length, 1 mm in width, longer than perianth but curved inward, anthers are 5 mm in length, 2 mm in width, attachment is versatile, 202A in color, dehiscence is longitudinal, pollen is abundant and 15C in color.

*Fruit.*—Capsule, 3-chambered, about 6 cm in length, 1 cm in width, 144A to 138A in color.

*Seeds.*—About 25 seeds per capsule, about 1 cm in length and 4 mm in width, N186A in color.

I claim:

1. A new and distinct cultivar of *Hosta* plant named 'Cathedral Windows' as herein illustrated and described.

* * * * *